(12) United States Patent
Deason et al.

(10) Patent No.: US 7,635,942 B2
(45) Date of Patent: Dec. 22, 2009

(54) SENSOR APPARATUS

(75) Inventors: Vance A. Deason, Idaho Falls, ID (US); Kenneth L. Telschow, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 621 days.

(21) Appl. No.: 11/130,853

(22) Filed: May 16, 2005

(65) Prior Publication Data

US 2006/0255689 A1 Nov. 16, 2006

(51) Int. Cl.
H01L 41/08 (2006.01)

(52) U.S. Cl. .................. 310/338; 310/320

(58) Field of Classification Search ........ 310/320, 310/328, 338, 311; 73/649; 356/357–359, 356/502–503; H01L 41/08, 41/09; G01B 9/02
See application file for complete search history.

(56) References Cited

U.S. PATENT DOCUMENTS

| 5,719,324 | A | | 2/1998 | Thundat et al. | |
|---|---|---|---|---|---|
| 6,041,642 | A | | 3/2000 | Duncan | |
| 6,134,006 | A | * | 10/2000 | Telschow et al. | ............ 356/503 |
| 6,155,118 | A | * | 12/2000 | Deboni | ...................... 340/459 |
| 6,175,411 | B1 | | 1/2001 | Telschow et al. | |
| 6,401,540 | B1 | | 6/2002 | Deason et al. | |
| 6,486,962 | B1 | | 11/2002 | Telschow et al. | |
| 6,836,336 | B2 | | 12/2004 | Deason et al. | |
| 6,933,164 | B2 | | 8/2005 | Kubena | |
| 2003/0128366 | A1 | * | 7/2003 | Deason et al. | .............. 356/502 |

* cited by examiner

Primary Examiner—Walter Benson
Assistant Examiner—Karen B Addison
(74) Attorney, Agent, or Firm—TraskBritt

(57) ABSTRACT

A sensor apparatus and method for detecting an environmental factor is shown that includes an acoustic device that has a characteristic resonant vibrational frequency and mode pattern when exposed to a source of acoustic energy and, further, when exposed to an environmental factor, produces a different resonant vibrational frequency and/or mode pattern when exposed to the same source of acoustic energy.

26 Claims, 5 Drawing Sheets

US 7,635,942 B2

SENSOR APPARATUS

GOVERNMENT RIGHTS

This invention was made with government support under Contract No. DE-AC07-05ID14517 awarded by the United States Department of Energy. The government has certain rights in the invention.

TECHNICAL FIELD

The present invention relates to a sensor apparatus and a method for detecting environmental factors and, more specifically, to an acoustic device that produces different resonant vibrational frequencies and/or modal patterns following exposure of the acoustic device to a given environmental factor and to an arrangement that is operable for reading out an array of such acoustic device sensors.

BACKGROUND

The prior art is replete with numerous examples of material inspection systems and other devices such as seen in U.S. Pat. Nos. 6,134,006, 6,175,411, 6,401,540, 6,486,962, and 6,836,336, which are useful for imaging traveling or resonant waves in a medium. Heretofore, these devices have been used to investigate the microstructural form and composition of an object. Further, many manufacturers have begun manufacturing and marketing various "microassay kits" that are utilized to detect various materials, including chemicals and biological organisms. These microassay kits, as a general matter, can usually be rapidly processed and permit the use of smaller quantities of analytes in the processing of same. A further parallel effort has been undertaken to provide arrays of microsensors that can rapidly detect the presence of a wide range of analytes. An example of this type of approach is the "lab on a chip" approach. These devices, after use, are often read out or interpreted by using a microscope. Typically, a color change in the device will indicate the presence of a substance or organism to be detected. This method can be implemented manually or by an automated image analysis.

As the size and complexity of these prior art arrays increase, the problems of accurately reading the data produced from these complex arrays has become increasingly difficult. Furthermore, in the fabrication of the microsensor arrays that utilize various electronic sensors, the ability to accurately read or gather a useful and accurate electrical output from the various electric sensors becomes increasingly difficult as the electrical wiring density increases. As could be expected, an increased wire density leads to "cross-talk" between adjacent electrical conductors that may be coupled to different electrical sensors in the same array.

A sensor apparatus and method for detecting various environmental factors that avoids the shortcomings attendant with the prior art practices utilized heretofore is the subject matter of the present application.

SUMMARY

Therefore, one aspect of the present invention relates to a sensor apparatus that includes an acoustic device that has a characteristic resonant vibrational frequency and mode pattern when exposed to a source of acoustic energy and, further, when exposed to an environmental factor, produces a different resonant vibrational frequency and/or mode pattern when exposed to the same source of acoustic energy.

Another aspect of the present invention is to provide an array that includes a plurality of acoustic devices that are operable to change their respective acoustic response when exposed to an environmental factor and an imaging assembly associated with the array of acoustic devices, which is useful in reading, measuring, or otherwise detecting changes in the acoustic response of the plurality of the respective acoustic devices after they have been exposed to the environmental factor.

Another aspect of the present invention relates to a sensor apparatus that includes an acoustic device that has a characteristic resonant vibrational frequency and mode pattern when exposed to acoustic energy; an assembly for transmitting acoustic energy to the acoustic device; a source of acoustic energy of a given frequency that is supplied to the acoustic device; and an assembly for imaging the acoustic device to determine the resonant vibrational frequency and/or modal pattern of the acoustic device when the acoustic device is exposed to the source of acoustic energy.

Still further, another aspect of the present invention relates to a method for detecting an environmental factor that includes the steps of providing an acoustic device having an acoustic property that includes a characteristic resonant vibrational frequency and mode pattern when exposed to acoustic energy; exposing the acoustic device to an environment that has an environmental factor to be detected, wherein the acoustic property of the acoustic device changes following the exposure of the acoustic device to the environmental factor; supplying a source of acoustic energy to the acoustic device; imaging the acoustic device following exposure of the acoustic device to the environmental factor while supplying the source of acoustic energy to the acoustic device; and determining whether the resonant frequency and mode pattern of the acoustic device has changed as a result of exposure to the environmental factor.

These and other aspects of the present invention will be described in greater detail hereinafter.

BRIEF DESCRIPTION OF THE DRAWINGS

Preferred embodiments of the invention are described below with reference to the following accompanying drawings.

DETAILED DESCRIPTION

This disclosure of the invention is submitted in furtherance of the constitutional purposes of the U.S. Patent Laws "to promote the progress of science and useful arts" (Article 1, Section 8).

Figure 1:
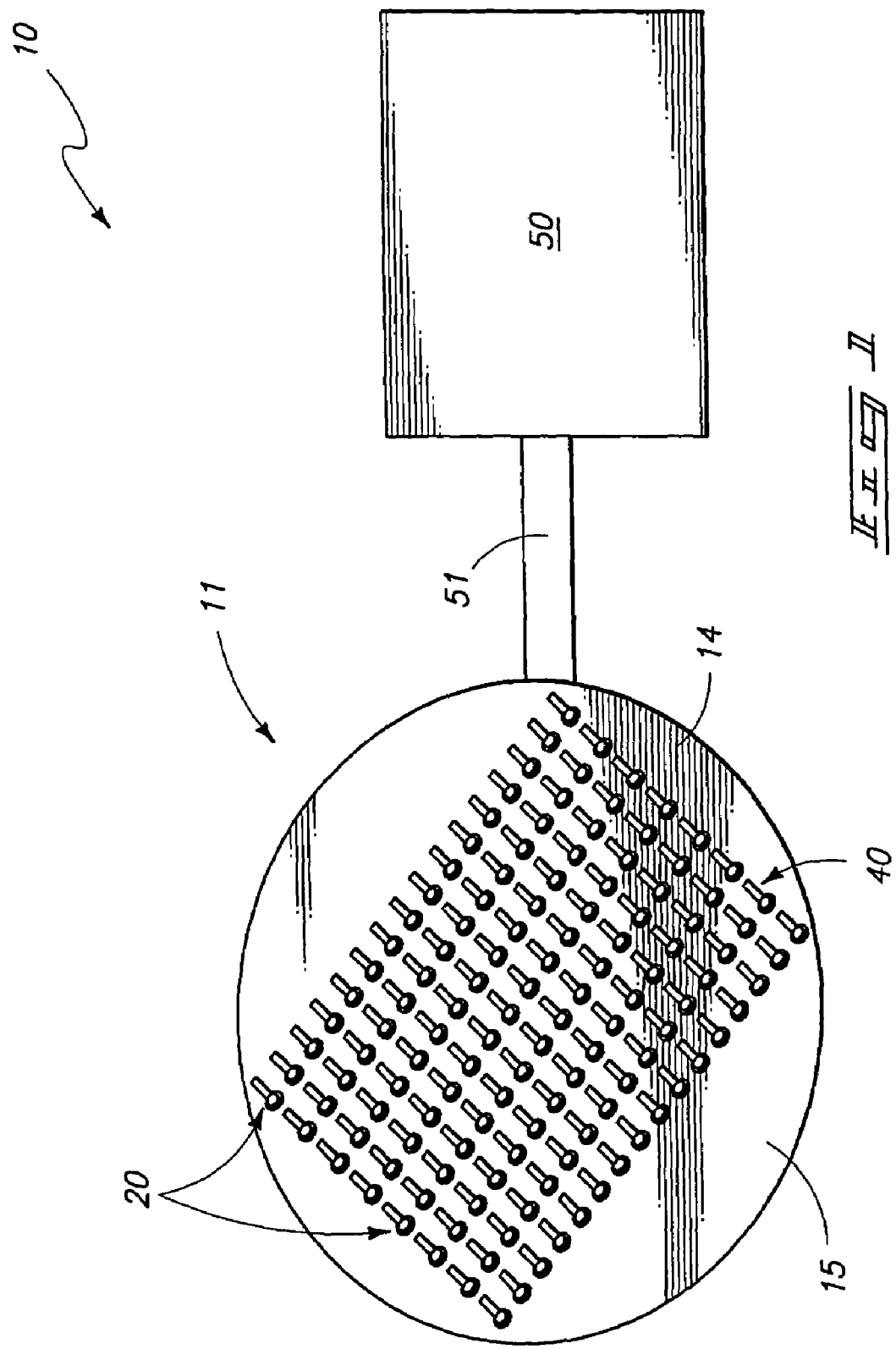
FIG. 1 is a greatly simplified depiction of a first form of a sensor apparatus of the present invention.
Figure 2:
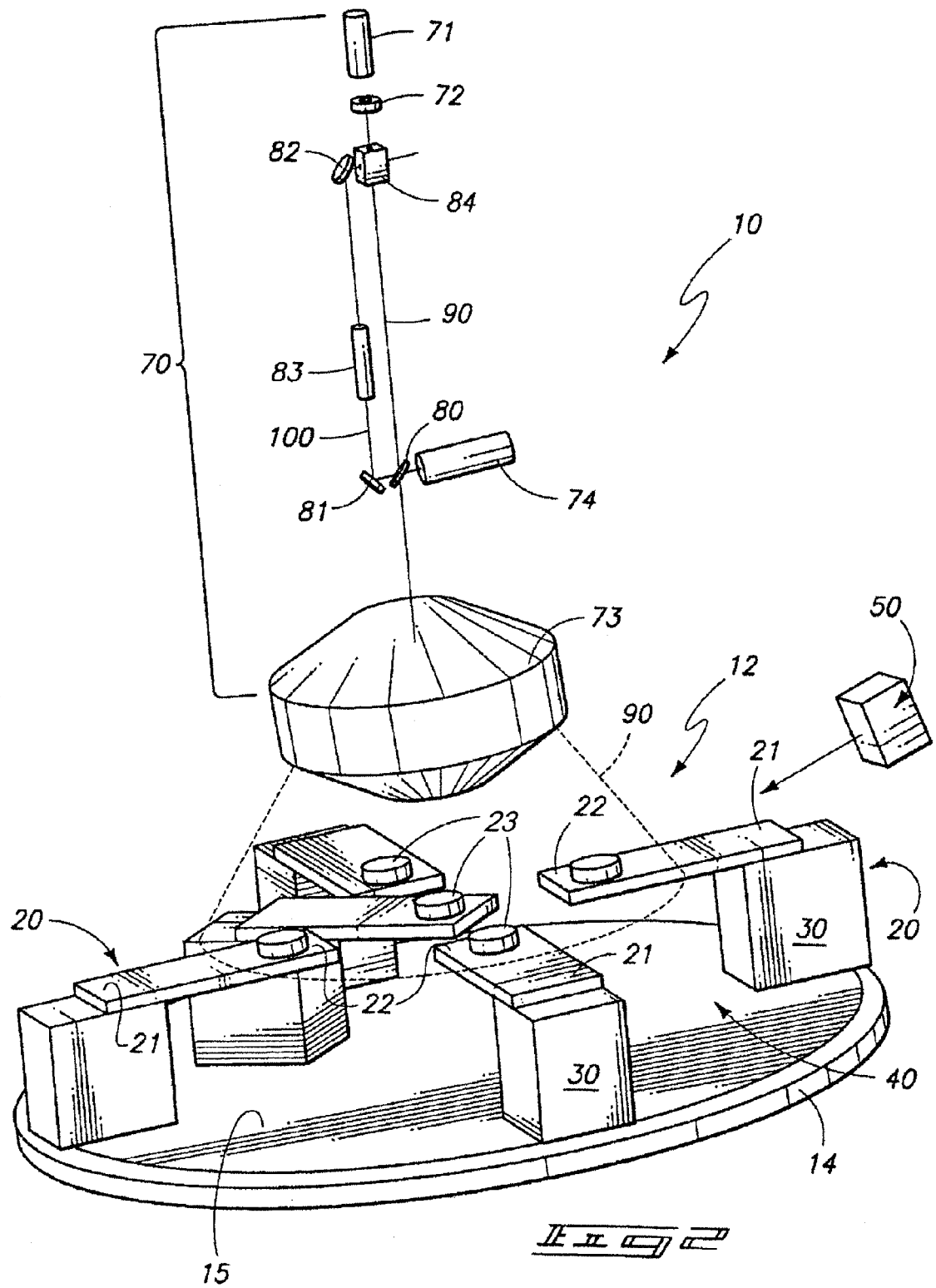
FIG. 2 is a greatly simplified graphical depiction of a second form of a sensor apparatus of the present invention.

The sensor apparatus of the present invention and the methodology for detecting an environmental factor is best understood by numeral 10 in FIG. 1 and following. As seen therein, the sensor apparatus 10 has first, second and third forms that are generally indicated by the numerals 11, 12 and 13. Referring now to FIG. 1, it will be seen that the sensor apparatus 10 has an underlying supporting surface or substrate 14 that has an upwardly facing surface 15. Mounted on the upwardly facing surface 15 is a plurality of acoustic devices here depicted as consecutive rows of individual cantilevered members, which are generally indicated by numeral 20. As seen most clearly by reference to FIG. 2, a second form of the invention is shown, whereby the cantilevered members 20 are oriented in another arrangement, each of the cantilevered members 20 having a first end 21 and a distal second end 22. Mounted on the second end 22 is an environmentally sensitive surface 23 that, when exposed to an environmental factor, may subsequently experience a change in thickness, damping, stiffness, Young's modulus, dimension, material properties such as elasticity, for example, and/or combinations thereof. While only a small region of the distal end is covered by the environmentally sensitive surface or coating, it should be recognized that the entire surface area between the first and second ends 21 and 22, respectively, may be covered by the environmentally sensitive surfaces 23. The cantilevered member 20 is held in spaced relation relative to the upwardly facing surface 15 by a support member 30. As seen in FIGS. 1-4, for example, the plurality of acoustic devices can be positioned in an array 40, as seen in FIGS. 1 and 2, for example, that are operable to respond to different environmental factors as will be discussed in greater detail hereinafter. In the arrangement as seen in FIG. 1 and following, it should be understood that the first, second and third forms of the invention 11, 12 and 13, respectively, each include at least one acoustic device that has a characteristic resonant vibrational frequency and mode pattern when exposed to a source of acoustic energy, which is generally indicated by numeral 50. Further, when exposed or following exposure to an environmental factor, as will be described below, these same acoustic devices as understood in the first, second and third forms of the invention 11, 12 and 13 produce a different resonant vibrational frequency and/or mode pattern when subsequently exposed to the same source of acoustic energy 50. This is illustrated most clearly by a study of FIGS. 5, 6, 7A and 7B, respectively.

In the arrangement as seen with respect to the first, second and third forms of the invention 11, 12 and 13, which are generally graphically depicted, it will be appreciated that the acoustic device selected, such as cantilevered member 20, may be selected from the group that includes quartz crystal microbalances, surface acoustic wave transducers, and thin film bulk, linear, and/or torsional acoustic resonators. Yet further, the environmental factor that the first, second and third forms of the invention 11, 12, and 13 can detect are selected from the non-limiting group comprising biological, chemical, thermal, acoustic, electromagnetic, and/or combinations thereof. In some instances, the acoustic device as shown in the several forms of the invention may increase in mass following exposure to the environmental factor. On the other hand, various forms of the invention may be designed such that the acoustic device may experience a decrease in mass following exposure to the environmental factor(s) discussed above. In any event, the acoustic device selected, as may be provided in the first, second and third forms 11, 12 and 13, experience physical changes following the exposure to the environmental factor. These changes may result, as noted above, in changes to the mass, thickness, damping, stiffness, Young's modulus of the acoustic device, and/or combinations thereof. As noted, when the acoustic device is subsequently exposed to the same source of acoustic energy, it produces a different resonant vibrational frequency or mode pattern that can be visually detected and that conclusively demonstrates the presence of the environmental factor. This is clearly illustrated in FIGS. 7A and 7B, for example. This arrangement can also be calibrated to indicate the quantity of the environmental factor that was exposed to apparatus 10.

Figure 5:
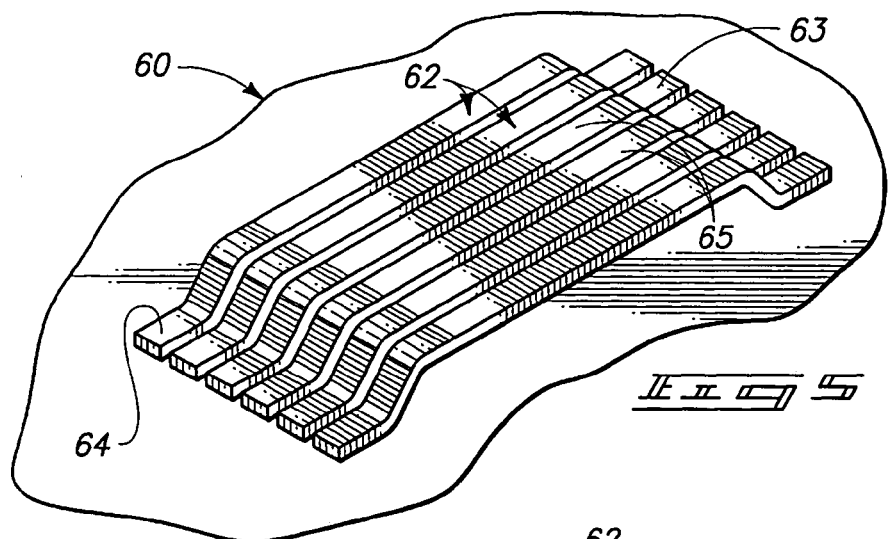
FIG. 5 is a greatly simplified and enlarged view of a portion of the third form of the sensor apparatus as seen in FIG. 4.
Figure 6:
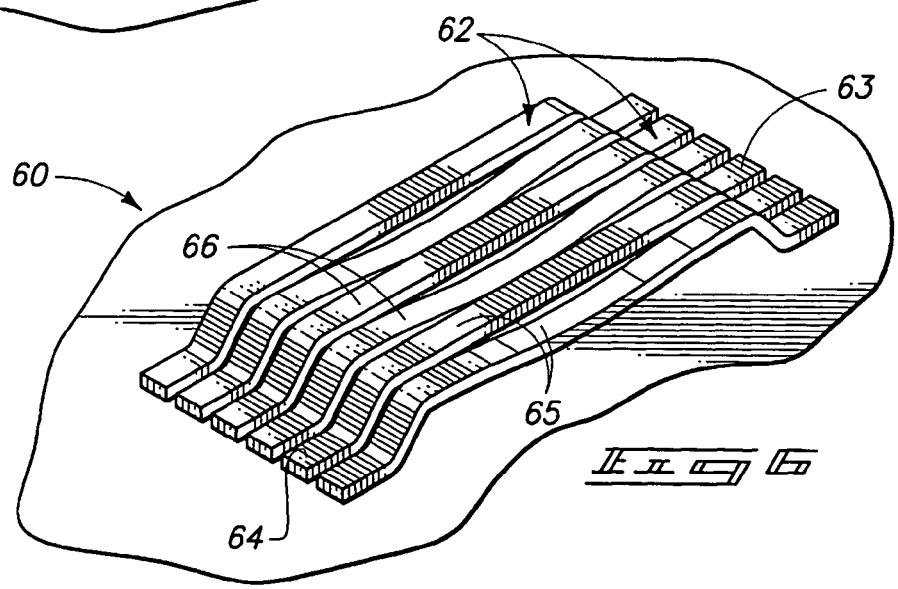
FIG. 6 is a perspective, greatly enlarged view of a portion of the sensor apparatus as seen in FIG. 5 that shows a response of the third form of the sensor apparatus after being exposed to an environmental factor.

In the arrangement as seen in FIGS. 1 and 5, for example, it should be understood that the several different acoustic devices as may be seen in the first, second and third forms of the invention 11, 12 and 13 may be placed into an array 40, wherein each of the plurality of acoustic devices is operable to respond to different environmental factors that can be read or otherwise substantially simultaneously detected. As should be understood, the source of acoustic energy 50 may be provided or otherwise supplied to the first, second and third forms of the invention 11, 12 and 13 at a single frequency, or may be provided at a plurality of frequencies. Still further, the source of acoustic energy 50 may be supplied by the ambient environment. Additionally, it should be understood that the environmentally sensitive surface 23 may comprise a commercially produced molecularly imprinted polymer that has an affinity for, and/or bonds to, a specific organic or inorganic chemical, microorganism, or biological material. In the arrangements as illustrated, the source of acoustic energy 50 may be derived from an energy source that is selected from the non-limiting group including, but not limited to, electrostatic, capacitive, thermal, optical, acoustic, magnetic, piezoelectric, mechanical, and/or combinations thereof. Generally, in the arrangement as shown, any source of acoustic energy 50 may be useful in the practice of the present invention.

As seen in FIG. 1, the first form of the invention 11 includes a plurality of these acoustic devices, here illustrated as the cantilevered members 20, which are positioned in consecutive linear rows. The individual cantilevered members 20 may be rendered operable to detect a single environmental factor or multiple environmental factors all from the same array 40.

Figure 4:
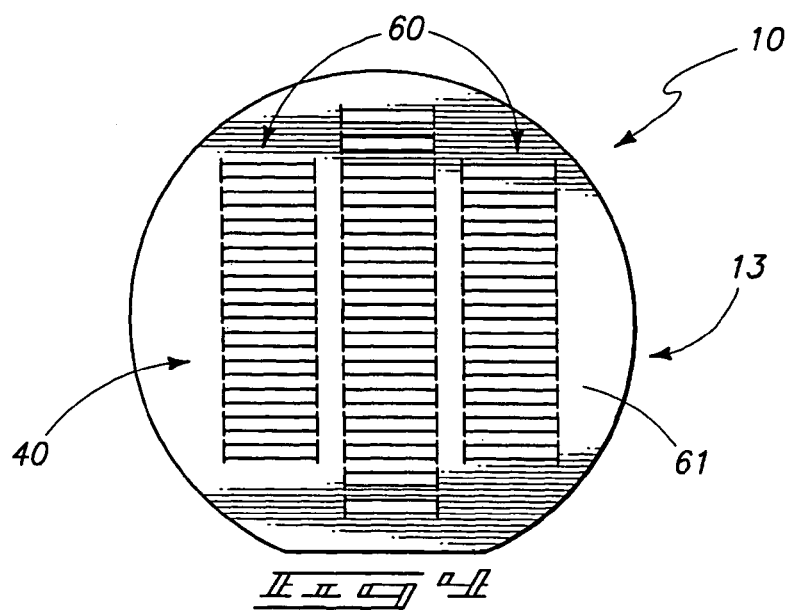
FIG. 4 is a plan view of a third form of a sensor apparatus of the present invention.
Figure 7A:
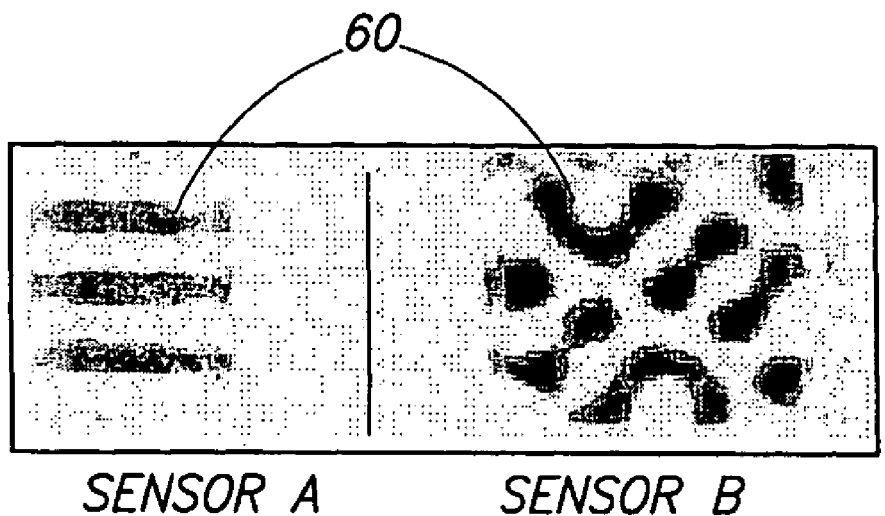
FIG. 7A is a depiction of a pair of sensors having a thin film bulk resonator design that illustrates a mode pattern displayed by the respective sensor when exposed to acoustic energy having a frequency of 21.006467 MHz and before exposure to an environmental factor to be detected.
Figure 7B:
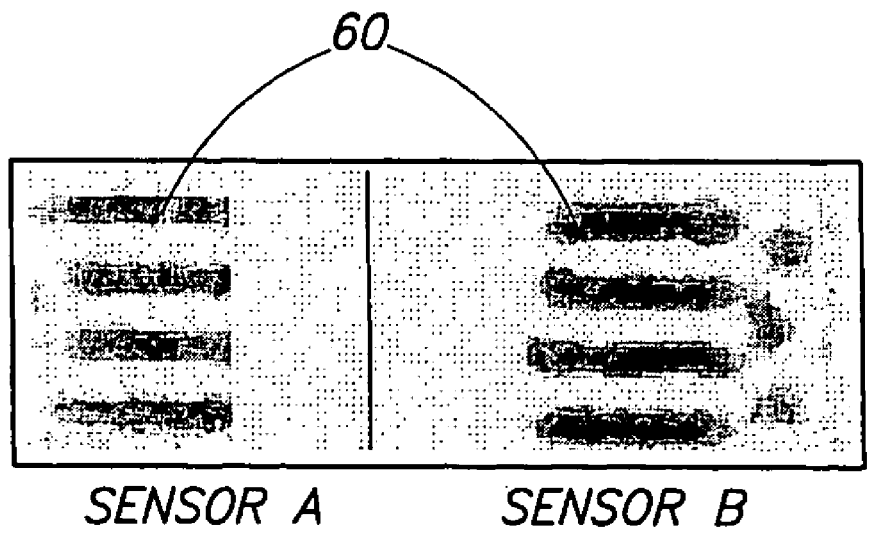
FIG. 7B is a depiction of the same pair of sensors having a thin film bulk resonator design as seen in FIG. 7A, but illustrating the mode pattern displayed by each respective sensor when exposed to acoustic energy having a frequency of 21.006200 MHz and following exposure to an environmental factor to be detected.

As will be discussed below and by reference to FIGS. 7A and 7B, it should be understood that the sensors may be disposed in a side-by-side orientation, which are individually operable to respond to different environmental factors. Referring now to FIG. 4, the third form 13 of the sensor apparatus 10 is shown, which includes groups of acoustic sensors 60 that again, like the first and second forms 11 and 12 of the sensor apparatus 10, are operable to detect various environmental factors that might be exposed to same. The groups of acoustic sensors 60 are positioned on a supporting substrate 61 and are made up of individual acoustic sensors 62, which are disposed in spaced relationship one to the other shown in FIG. 5. As shown therein, the individual acoustic sensors 62 have a first end 63 and an opposite second end 64 that are affixed to the supporting substrate 61. The individual acoustic sensors 62 further have an upwardly facing deformable surface 65, which has been treated or otherwise coated, or supplied with an environmentally sensitive surface 66, such as molecular imprinted polymers as earlier discussed with respect to the first form of the invention 11. As shown in FIGS. 5, 6, 7A and 7B, the groups of acoustic sensors 60 are exposed to the environmental factors as earlier described and are operable to change their acoustic characteristics similar to that described with respect to the first form of the invention 11; that is, once exposed to the environmental factor, they produce a different resonant vibrational frequency and/or mode pattern when exposed to the same source of acoustic energy such as source 50. As should be understood, an assembly for transmitting the given acoustic energy to the acoustic device 51 is provided and is only generally illustrated in FIG. 1. It will be seen by reference to FIG. 6, that the plurality of acoustic sensors 60, as illustrated therein, has been previously exposed to an environmental factor that has caused the mass of the individual acoustic sensors 62 to change, thereby deforming the deformable surface 65. This results in a change in the acoustic characteristics of these same devices once they are exposed to a source of acoustic energy such as source 50.

Referring now to FIG. 7A, individual groups of acoustic sensors 60 are shown that have been rendered operable to detect a selected environmental factor. FIG. 7A depicts an actual mode pattern that is displayed from pairs of micromachined vibratory thin film bulk resonator structures when these same acoustic devices are exposed to a source of acoustic energy 50, which has a frequency of 21.006467 MHz, and prior to the exposure of the acoustic sensors 60 to the selected environmental factor. Referring now to FIG. 7B, the same groups of acoustic sensors 60 are shown that illustrate the mode pattern of the same groups of acoustic sensors 60 following exposure to the selected environmental factor and when exposed to the source of acoustic energy 50 having a different frequency of about 21.006200 MHz. As can be seen, the change in the mode pattern as illustrated by a comparison of FIGS. 7A and 7B demonstrates that the groups of sensors 60 have been exposed to the selected environmental factor.

Figure 3:
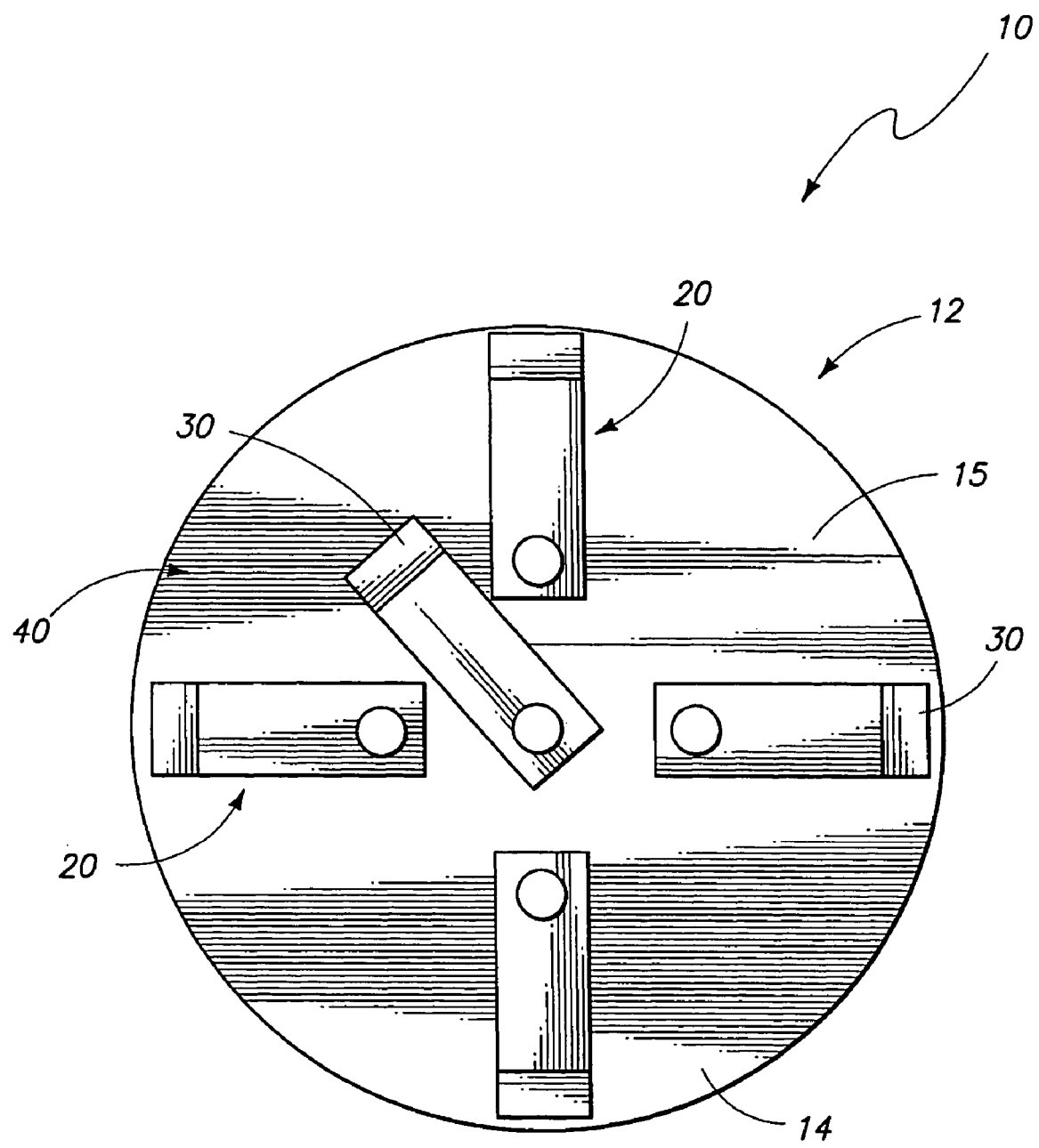
FIG. 3 is a plan view of the second form of the sensor apparatus as seen in FIG. 2.

FIGS. 2 and 3 show the second form 12 of the sensor apparatus 10 including a plurality of acoustic devices, as illustrated, that include various cantilevered members generally indicated by the numeral 20. As best seen by a study of FIG. 2, the sensor apparatus 10 includes an assembly 70 for imaging an acoustic device, such as cantilevered member 20, following the exposure of the acoustic device to the environmental factor, as earlier described, and while the acoustic device is being exposed to the source of acoustic energy 50 to determine the resonant frequency and/or modal pattern of the acoustic devices involved. The assembly 70 for imaging the acoustic devices produces a visibly discernible image of the mode pattern of the respective acoustic devices as seen most clearly by reference to FIGS. 7A and 7B, respectively. The assembly 70 for imaging an acoustic device following the exposure of the acoustic device(s) to the environmental factor is shown in a greatly simplified arrangement. Other devices that will work with equal success are those shown in U.S. Pat. Nos. 6,836,336, 6,134,006, 6,175,411 and 6,486,962, the teachings of which are all incorporated by reference herein. For ease of illustration, however, the assembly 70 for imaging the acoustic device generally includes a digital camera or other video device 71 that is capable of forming a discernible video image of the respective acoustic devices from coherent light that is directed at and reflected from the acoustic device (FIGS. 7A and 7B). The digital camera or video device 71 is operably coupled with a camera lens, which is generally indicated by the numeral 72. Positioned in spaced relation relative to the camera lens 72 is an imaging lens 73. Further, a laser 74 is positioned in spaced relation therebetween the digital camera 71 and the imaging lens 73. The laser 74, in the present arrangement, is a non-contacting, coherent light-emitting device that directs a beam of light, as will be discussed below, at the plurality of vibratory members 20. The assembly 70 further includes a beam splitter 80, which is positioned in spaced relation relative to the laser 74. Still further, first and second reflecting mirrors 81 and 82 are provided to direct the emitted beam of light along a given course of travel, as will be discussed below. The imaging assembly 70 further includes a reference beam modulator 83. Additionally, a photorefractive material 84 is provided.

As seen in FIG. 2, it is understood that the laser 74 produces a first object light beam 90 and a second reference light beam, which is generally indicated by the numeral 100. In the arrangement as seen in FIG. 2, the imaging lens 73 is configured to focus the object beam 90, as shown by dashed lines, following reflection from the cantilevered members 20, which are in an array, onto a desired location of the photorefractive material 84. The imaging lens 73 has a conventional design presently understood in the art. In the arrangement as shown, and upon being reflected off the plurality of cantilevered members 20, the object beam 90 has been impressed with information defining the given vibrational displacement amplitude and vibrational phase of the plurality of acoustic sensors that are shown in that view. The object beam 90 is combined to interfere with the reference beam 100, which takes place within the photorefractive material 84 by way of a two-wave anisotropic self-diffraction, with or without polarization rotation. An equivalent arrangement using a four-wave anisotropic self diffraction could also be employed with equal success. In the arrangement as seen in FIG. 2, the object and reference beams 90 and 100 are mutually coherent so as to interfere within the photorefractive material 84. The reference beam modulator 83 operates on reference beam 100 to produce a phase-modulated reference beam. The phase-modulated reference beam and the reflected object beam 90 interfere within and pass through the photorefractive material 84 so as to create a space-charged field having a magnitude that is directly proportional to the vibration displacement. The space-charged field produces an index of refraction grating by the electro-optic effect that contains information of the vibrational state of the plurality of acoustic devices or cantilevered members 20. The photorefractive material 84 has a given response time wherein the induced grating within the photorefractive material 84 passes the reflected object beam 90 and reference beam 100. Object beam 90 and reference beam 100 interfere within the photorefractive material 84 to create a space-charged field and resulting induced grating, which develops within the response time of the photorefractive material 84. In this regard, the object beam 90 is reflected off of the vibrating acoustic devices or cantilevered members 20 having a vibration displacement amplitude and a vibration phase. The photorefractive material 84 passes the reflected object beam 90 and the reference beam 100 such that their interference therein creates a space-charged field-induced grating having a diffraction efficiency that is directly proportional to the vibration displacement for small amplitudes. This displacement of the acoustic devices or cantilevered members 20 that is induced by the source of acoustic energy 50 is then captured as a digital video image in the digital camera or video device 71 that is provided. The results are seen in FIGS. 7A and 7B. As illustrated in FIG. 2, it will be seen that the assembly 70 for imaging the acoustic device is operable to image a plurality of acoustic devices substantially simultaneously and without the shortcomings attendant with the earlier prior art practices that have been described earlier in this application.

The operation of the described embodiment of the present invention is believed to be readily apparent and is briefly summarized at this point.

As seen in the various drawings, the sensor apparatus 10 of the present invention includes an acoustic device, such as member 20 or sensor 60, that has a characteristic resonant vibrational frequency and mode pattern when exposed to a source of acoustic energy 50. Still further, the source of acoustic energy 50 has a given frequency that is supplied to the acoustic devices noted. In addition to the foregoing, an assembly 70 for imaging the acoustic device is provided. The imaging device is operable to determine the resonant frequency and/or modal pattern of the acoustic sensor 60 when the acoustic device is exposed to the source of acoustic energy 50. As seen in the drawings, a plurality of acoustic devices may be deployed in an array 40. As seen in FIG. 2, the assembly 70 for imaging the acoustic device may image each of the plurality of acoustic devices substantially simultaneously. As earlier discussed, the source of acoustic energy 50 may be a separate source, or may, in the alternative, be provided by the ambient environment. As illustrated, the acoustic device has a surface area (not shown) that may be treated to bond to a specific chemical or biological material or otherwise react to another environmental factor, which may be physical, material or anything of whatever nature that is in the environment. For example, when a biological material bonds to same, the acoustic device, such as cantilevered member 20, experiences a change in its physical characteristics (an increasing mass) and that, at least in part, influences an acoustic response of the cantilevered member 20. The change in the acoustic response may include, at least in part, a resulting different resonant vibrational frequency and/or mode when exposed to the source of acoustic energy 50. As earlier discussed, the changes in the physical characteristics of the acoustic device that effects the acoustic response of the acoustic device relates to a change in mass, thickness, stiffness, damping, Young's modulus, dimension, material properties such as elasticity, for example, and/or combinations thereof. The surface area of the acoustic device may mount, for example, in one form, a molecularly imprinted polymer that has an affinity for, and/or bonds to, the specific chemical or biological materials that comprise, at least in part, the environmental factor that is to be detected. As earlier discussed, the source of acoustic energy 50 may be derived from nearly any available source of acoustic energy, such as, for example, electrostatic, capacitive, thermal, optical, acoustic, magnetic, piezoelectric, mechanical, and/or combinations thereof. In the invention as shown, an assembly 70 for imaging the acoustic device is provided that includes, without limitation, a non-contacting, coherent light-emitting device, such as the laser 74, that directs first object light beam 90 at the plurality of vibrating cantilevered members 20 that is reflected from same and a photorefractive material 84 that could conceivably be incorporated into a dynamic photorefractive holographic interferometer. Further, the imaging assembly 70 includes a video assembly that may comprise a digital camera 71 for capturing the object light beam 90 and that produces a video image of the vibrational movements of each of the cantilevered members 20. As shown in FIG. 2, the assembly 70 for imaging the acoustic device is not operably coupled with the respective cantilevered member 20. Still further, the several cantilevered members 20 may be vibrated by the source of acoustic energy 50 at a single resonant frequency, at multiple frequencies, and/or moved or otherwise swept through a range of frequencies, depending upon the circumstances. In sensor apparatus 10, the plurality of acoustic devices is vibrated by a source of acoustic energy 50 at a resonant frequency that lies within a range of about 100 Hz to about 5 GHz. As seen in the various drawings, the surface area of any array 40 is typically less than about 100 square millimeters, although it is conceivable that larger arrays could be constructed.

In the arrangement as shown, the plurality of acoustic devices as seen in the various forms of the invention 11, 12 and 13 has an intrinsic response to an environmental factor, as earlier described, which results in a different resonant vibrational frequency and/or mode when the acoustic device is exposed to the source of acoustic energy 50.

In the drawings, a method for detecting an environmental factor is shown that includes the steps of providing an acoustic device having an acoustic property including a characteristic resonant vibrational frequency and mode pattern when exposed to a source of acoustic energy 50. The method further includes a step of exposing the acoustic device to an environment that has an environmental factor to be detected, wherein the acoustic property and/or resulting acoustic response of the acoustic device changes following the exposure of the acoustic device to the environmental factor. The method for detecting an environmental factor further includes the step of supplying a source of acoustic energy 50 to the acoustic device, and a further step of imaging the acoustic device following the exposure of the acoustic device to the environmental factor and while supplying the source of acoustic energy 50 to the acoustic device. The methodology of the present invention further includes a step of determining whether the resonant frequency and/or mode pattern of the acoustic device has been changed as a result of exposure to the environmental factor. As earlier described, the step of providing the acoustic device may further comprise a step of providing a plurality of acoustic devices, and arranging the plurality of acoustic devices in an array 40. As earlier noted, the environmental factor to be detected may comprise a plurality of different environmental factors that are selected from the group comprising biological, chemical, physical, material, thermal, acoustic, electromagnetic, and/or combinations thereof. In the arrangements as illustrated, the method for imaging the acoustic device further comprises the steps of directing and reflecting a beam of coherent light 90 off of the acoustic device and capturing a video image from a video device 71 of the vibrational movement of the several acoustic devices from the captured coherent light. In the arrangements as shown, the step of imaging the acoustic device further comprises imaging the plurality of acoustic devices substantially simultaneously.

Therefore, it will be seen that the present invention provides a convenient means whereby a plurality of environmental factors can be easily detected and readily read or identified from a microsensor array that is relatively small in size and convenient to use. The present sensor apparatus 10 can be used in a wide range of commercial and military applications and provides a convenient means for rapidly detecting possibly adverse environmental factors in a manner not possible heretofore. Still further, the present invention offers a novel methodology of reading arrays of variously designed sensors that are responsive to all manner of sources of vibrational or acoustic energy and that have been rendered useful in detecting any desired environmental factor as discussed above.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A sensor apparatus, comprising:
    at least one acoustic device exhibiting a characteristic resonant vibrational frequency and mode pattern when exposed to an acoustic energy, and when exposed to an environmental factor, exhibits at least one of a different resonant vibrational frequency and a different mode pattern when exposed to the acoustic energy; and
    an assembly for imaging the at least one acoustic device to determine at least one of the resonant vibrational frequency and mode pattern of the acoustic device when the acoustic device is exposed to acoustic energy.

2. The sensor apparatus of claim 1, wherein the at least one acoustic device is selected from at least one of quartz crystal microbalances, surface acoustic wave transducers, thin film bulk linear acoustic resonators and thin film bulk torsional acoustic resonators.

3. The sensor apparatus of claim 1, wherein the environmental factor is selected from at least one of biological, chemical, physical, material, thermal, acoustic, and electromagnetic.

4. The sensor apparatus of claim 1, wherein the at least one acoustic device experiences an increase in mass following exposure to the environmental factor.

5. The sensor apparatus of claim 1, wherein the at least one acoustic device experiences a decrease in mass following exposure to the environmental factor.

6. The sensor apparatus of claim 1, wherein the at least one acoustic device has acoustic properties which change following exposure of the at least one acoustic device to the environmental factor.

7. The sensor apparatus of claim 1, wherein the at least one acoustic device experiences a change in at least one of mass, thickness, damping, stiffness, Young's modulus, dimension, and material properties when exposed to the environmental factor.

8. The sensor apparatus of claim 1, further comprising a source adapted to provide acoustic energy at a single frequency.

9. The sensor apparatus of claim 1, further comprising a source adapted to provide acoustic energy at a plurality of frequencies.

10. The sensor apparatus of claim 9, wherein the source is adapted to sweep acoustic energy through the plurality of frequencies.

11. The sensor apparatus of claim 1, wherein the at least one acoustic device comprises a plurality of acoustic devices, wherein the plurality of acoustic devices are placed in an array, and wherein at least some of the plurality of acoustic devices of the array are operable to respond to different environmental factors.

12. The sensor apparatus of claim 1, further comprising an assembly for transmitting acoustic energy to the at least one acoustic device.

13. The sensor apparatus of claim 1, wherein the at least one acoustic device comprises a plurality of acoustic devices deployed in an array, wherein the assembly for imaging the at least one acoustic device is adapted to image each of the plurality of acoustic devices in the array at least substantially simultaneously.

14. The sensor apparatus of claim 1, wherein the acoustic energy is supplied by an ambient environment.

15. The sensor apparatus of claim 1, wherein the at least one acoustic device has a surface area treated to bond to a specific chemical or biological material, wherein the surface area when exposed to the specific chemical or biological material bonds thereto and experiences a change in its physical characteristics.

16. The sensor apparatus of claim 15, wherein the treated surface area of the at least one acoustic device comprises a molecularly imprinted polymer and/or analyte binding material that has an affinity for, and/or bonds to, the specific chemical or biological material.

17. The sensor apparatus of claim 1, further comprising an energy source for providing the acoustic energy selected from at least one of electrostatic, capacitive, thermal, optical, acoustic, magnetic, piezoelectric and mechanical.

18. The sensor apparatus of claim 1, wherein the assembly for imaging the at least one acoustic device comprises:
    non-contacting, coherent light-emitting device for directing a beam of light at the at least one acoustic device; and
    a dynamic photorefractive holographic interferometer and video assembly for capturing the light reflected from the at least one acoustic device and producing a video image of the vibrational mode pattern and movement of the acoustic device, wherein the non-contacting, coherent light-emitting device, dynamic photorefractive holographic interferometer, and video assembly are not operably coupled to the at least one acoustic device.

19. The sensor apparatus of claim 1, wherein the at least one acoustic device is vibrated by the acoustic energy at a resonant frequency that lies within a range of about 100 Hz to about 5 GHz.

20. The sensor apparatus of claim 1, wherein the at least one acoustic device comprises a plurality of acoustic devices arranged in an array, wherein the respective acoustic devices of the array each have a given mass and a surface area capable of bonding to a chemical and/or biological material, wherein the surface area of the array is less than about 100 square millimeters.

21. A sensor apparatus, comprising:
    at least one acoustic device comprising a resonant vibrational frequency and mode pattern when exposed to an acoustic energy, the at least one acoustic device configured to produce at least one of a different resonant vibrational frequency and a different mode pattern when exposed to an environmental factor and to the acoustic energy; and
    an assembly configured to image the at least one acoustic device to determine at least one of the resonant frequency and the modal pattern of the at least one acoustic device when exposed to the acoustic energy.

22. The sensor apparatus of claim 21, wherein the at least one acoustic device is configured to experience a change in at least one of mass, thickness, damping, stiffness, Young's modulus, dimension, and material properties when exposed to the environmental factor.

23. The sensor apparatus of claim 21, wherein the environmental factor comprises at least one environmental factor selected from the group comprising biological, chemical, physical, material, thermal, acoustic, and electromagnetic.

24. The sensor apparatus of claim 21, wherein the assembly configured to image the at least one acoustic device comprises:

a light emitting device configured to impinge a beam of light on at least a portion of the at least one acoustic device; and a video assembly configured to capture light reflected from the at least one acoustic device, and to produce at least one image of a vibrational movement of the at least one acoustic device.

25. The sensor apparatus of claim 24, wherein the assembly configured to image the at least one acoustic device further comprises a dynamic photorefractive holographic interferometer configured to capture the light reflected from the at least one acoustic device.

26. The sensor apparatus of claim 21, wherein the at least one acoustic device comprises a material disposed on at least a portion thereof, the material configured to bond to a specific chemical or biological material.

* * * * *

UNITED STATES PATENT AND TRADEMARK OFFICE
CERTIFICATE OF CORRECTION

PATENT NO. : 7,635,942 B2  Page 1 of 1
APPLICATION NO. : 11/130853
DATED : December 22, 2009
INVENTOR(S) : Deason et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1206 days.

Signed and Sealed this

Twenty-first Day of December, 2010

David J. Kappos
*Director of the United States Patent and Trademark Office*

UNITED STATES PATENT AND TRADEMARK OFFICE
CERTIFICATE OF CORRECTION

PATENT NO. : 7,635,942 B2  
APPLICATION NO. : 11/130853  
DATED : December 22, 2009  
INVENTOR(S) : Vance A. Deason and Kenneth L. Telschow Page 1 of 1

It is certified that error appears in the above-identified patent and that said Letters Patent is hereby corrected as shown below:

In the specification:
COLUMN 7, LINE 51, change "directs first" to --directs a first--

In the claims:
CLAIM 18, COLUMN 10, LINE 17, change "non-contacting," to --a non-contacting,--

Signed and Sealed this  
Twenty-sixth Day of February, 2013

Teresa Stanek Rea  
*Acting Director of the United States Patent and Trademark Office*